(12) United States Patent
Loebl et al.

(10) Patent No.: US 11,751,928 B2
(45) Date of Patent: *Sep. 12, 2023

(54) STIFF GUIDE WIRE WITH ANCHORING CONFIGURATION

(71) Applicant: SeaSpine, Inc., Carlsbad, CA (US)

(72) Inventors: Oded Loebl, Tel Mond (IL); Netanel Sharabani, Rishpon (IL)

(73) Assignee: SeaSpine, Inc., Carlsbad, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 17/132,818

(22) Filed: Dec. 23, 2020

(65) Prior Publication Data

US 2021/0138204 A1    May 13, 2021

Related U.S. Application Data

(63) Continuation of application No. 15/772,101, filed as application No. PCT/IL2016/051209 on Nov. 9, 2016, now Pat. No. 10,874,836.

(60) Provisional application No. 62/252,595, filed on Nov. 9, 2015.

(51) Int. Cl.
*A61B 17/88* (2006.01)
*A61M 25/09* (2006.01)
*A61M 25/04* (2006.01)
*A61B 17/84* (2006.01)

(52) U.S. Cl.
CPC ...... *A61B 17/8897* (2013.01); *A61B 17/8852* (2013.01); *A61M 25/04* (2013.01); *A61M 25/09* (2013.01); *A61M 25/09025* (2013.01); *A61B 17/844* (2013.01); *A61M 2025/09125* (2013.01)

(58) Field of Classification Search
CPC ........... A61M 25/09025; A61B 17/844; A61B 17/8852; A61B 17/8897
See application file for complete search history.

(56) References Cited

U.S. PATENT DOCUMENTS

2007/0239252 A1    10/2007    Hopkins et al.
2018/0311478 A1    11/2018    Loebl

FOREIGN PATENT DOCUMENTS

WO    2009108942 A1    9/2009
WO    2014165754 A1    10/2014

OTHER PUBLICATIONS

Israel Patent Office, International Search Report and Written Opinion for PCT/IL2016/051209 dated Feb. 6, 2017, 10 pages.

*Primary Examiner* — Andrew Yang
(74) *Attorney, Agent, or Firm* — Dinsmore & Shohl LLP

(57) ABSTRACT

A device (10) which serves as a stiff guide wire for surgical procedures includes a tube (12) having an internal channel, and a central rod (14) in close-fitting sliding engagement within the tube. The tips of the tube and the central rod are in rigid mechanical engagement or interconnection. A region of the tube (112) is longitudinally slotted to form deflectable strips (18) so that advancing of the tube (12) relative to central the rod (14) causes outward deflection of the strips (18) to form an anchoring configuration. The central rod (14) and the tube (12) together define a stiff guide wire preferably having a length-to-width ratio in excess of 100:1.

21 Claims, 10 Drawing Sheets

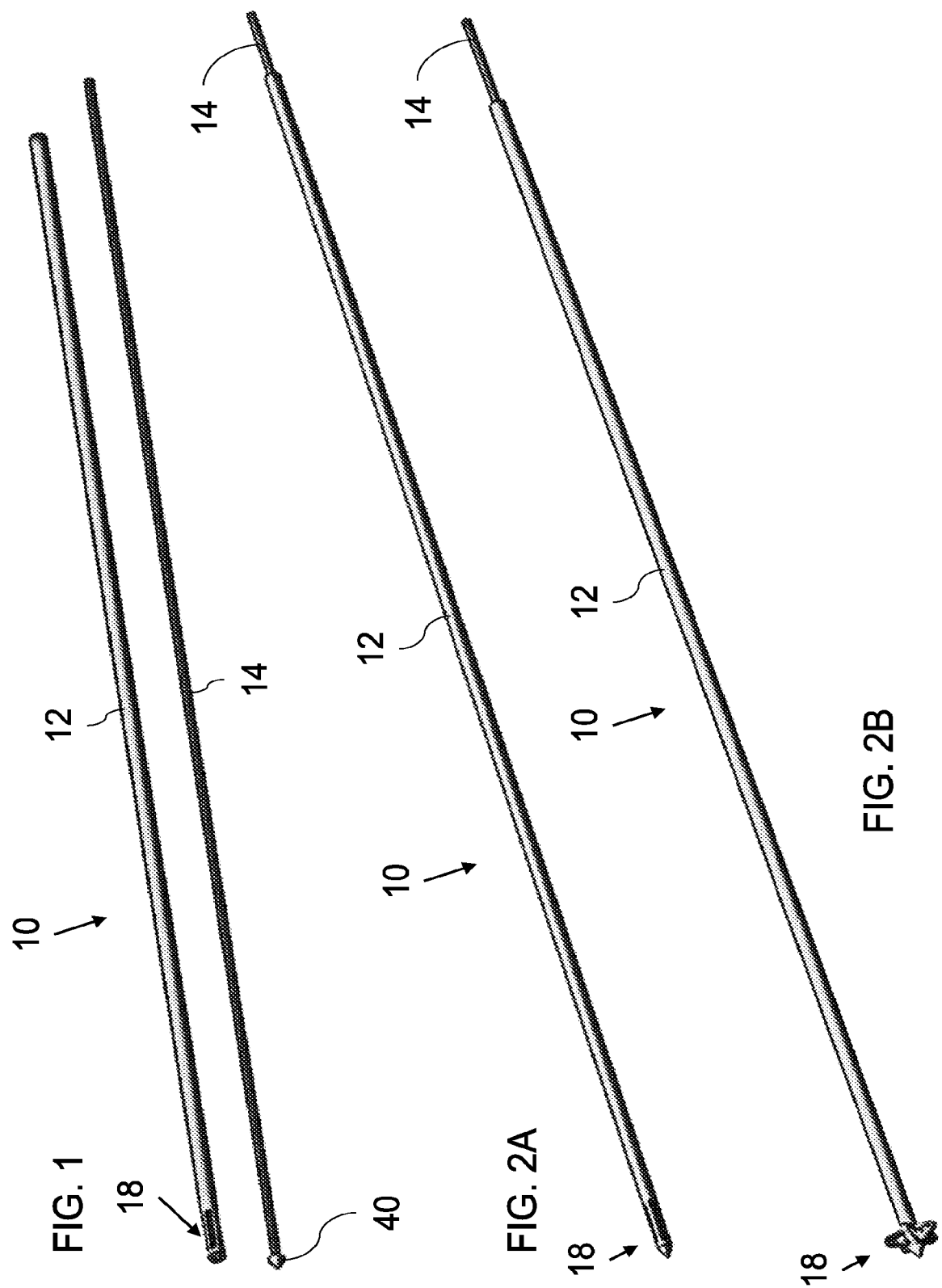

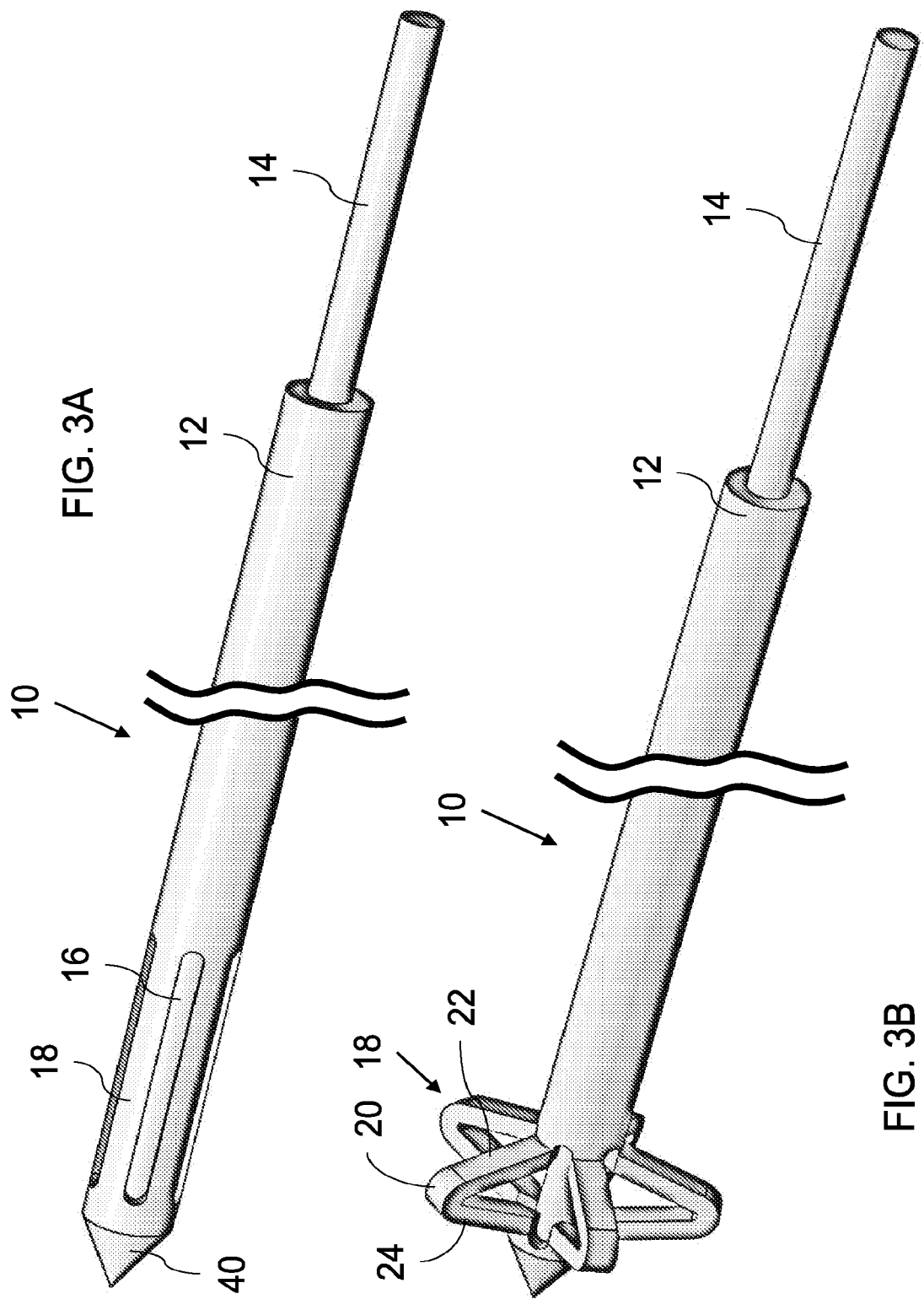

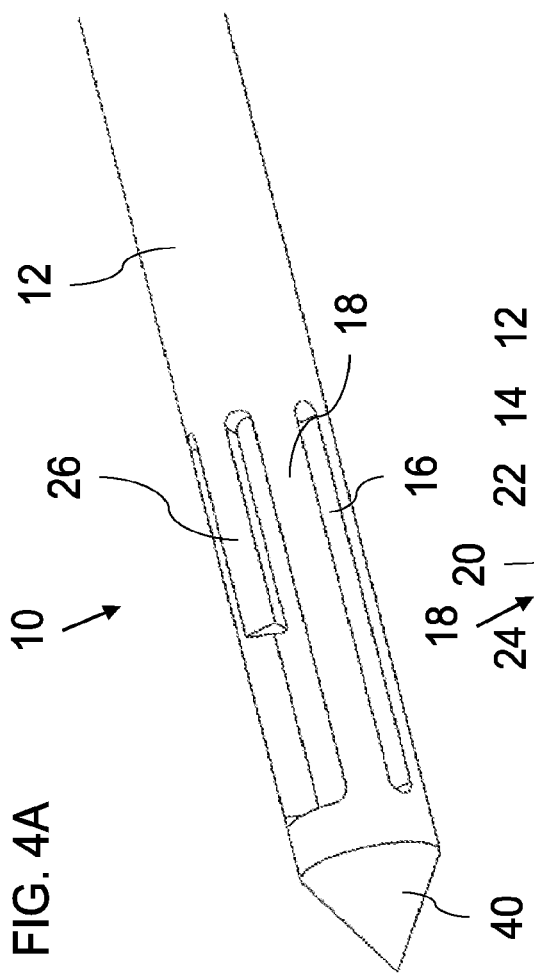
FIG. 4A
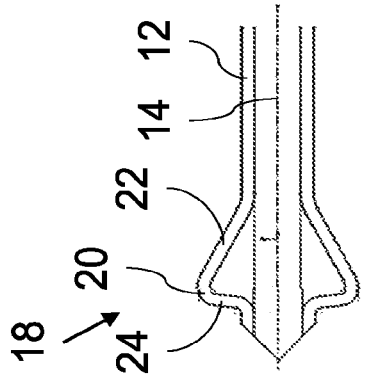
FIG. 4D
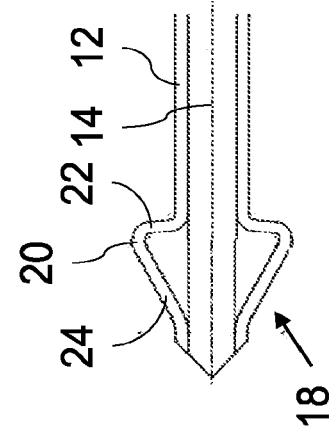
FIG. 4E
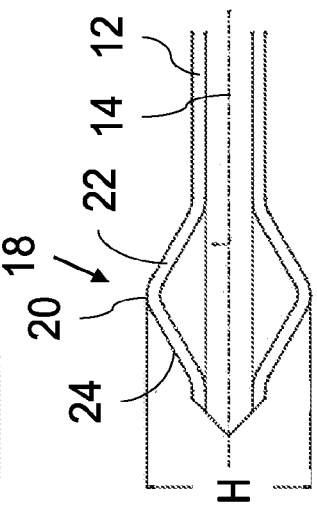
FIG. 4B
FIG. 4C

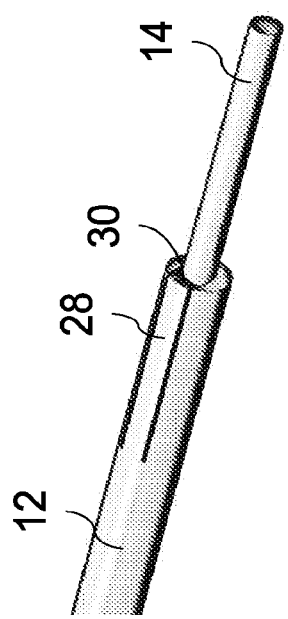 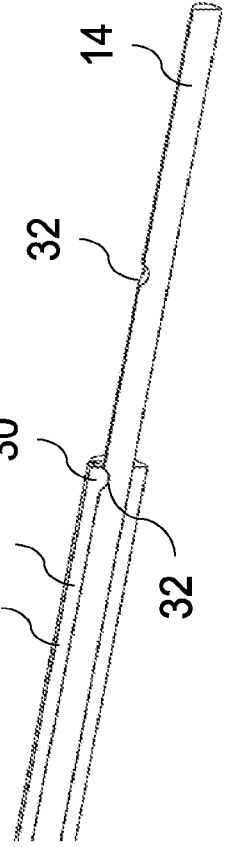
FIG. 6A  FIG. 6B  FIG. 6C

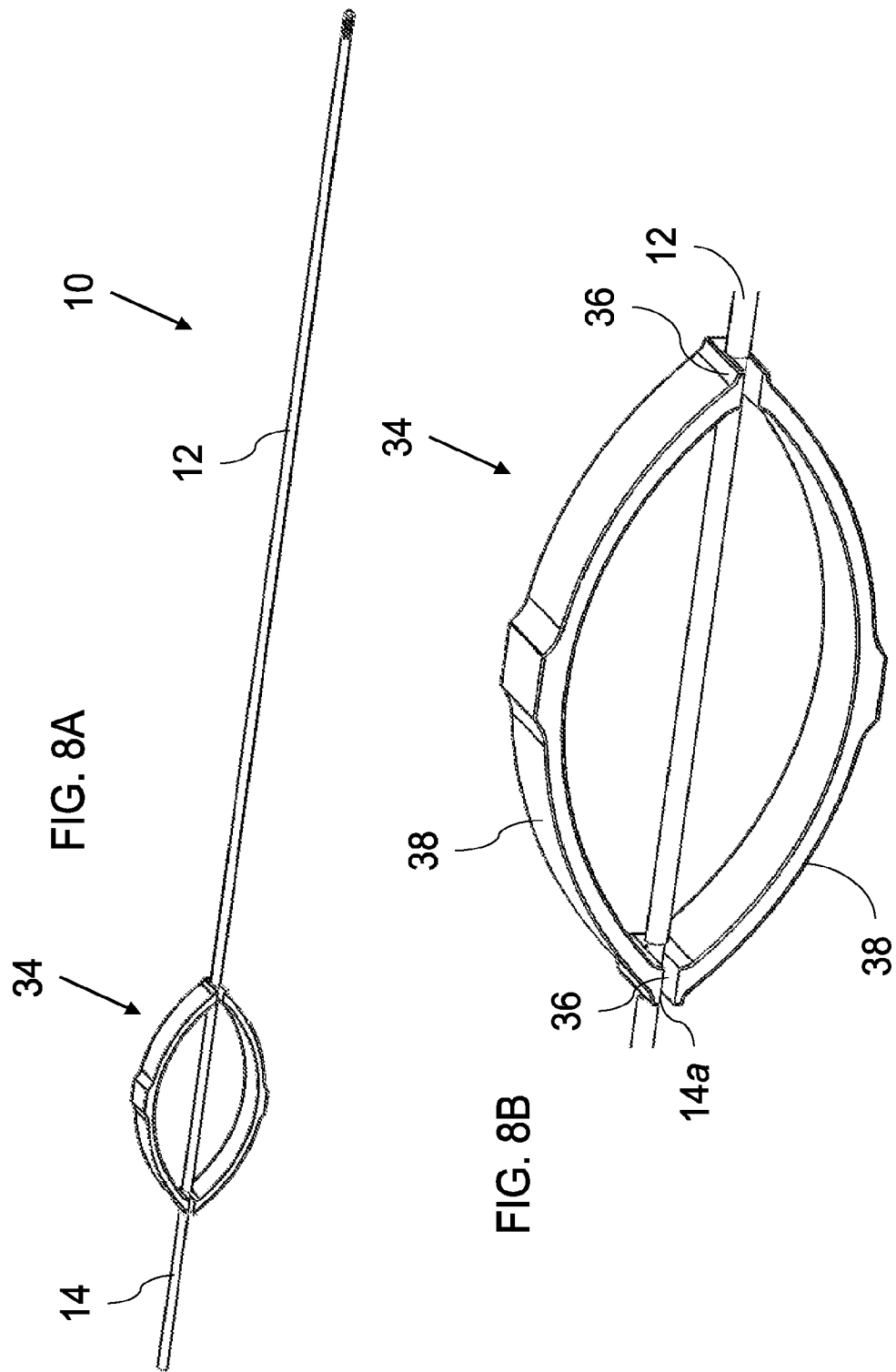

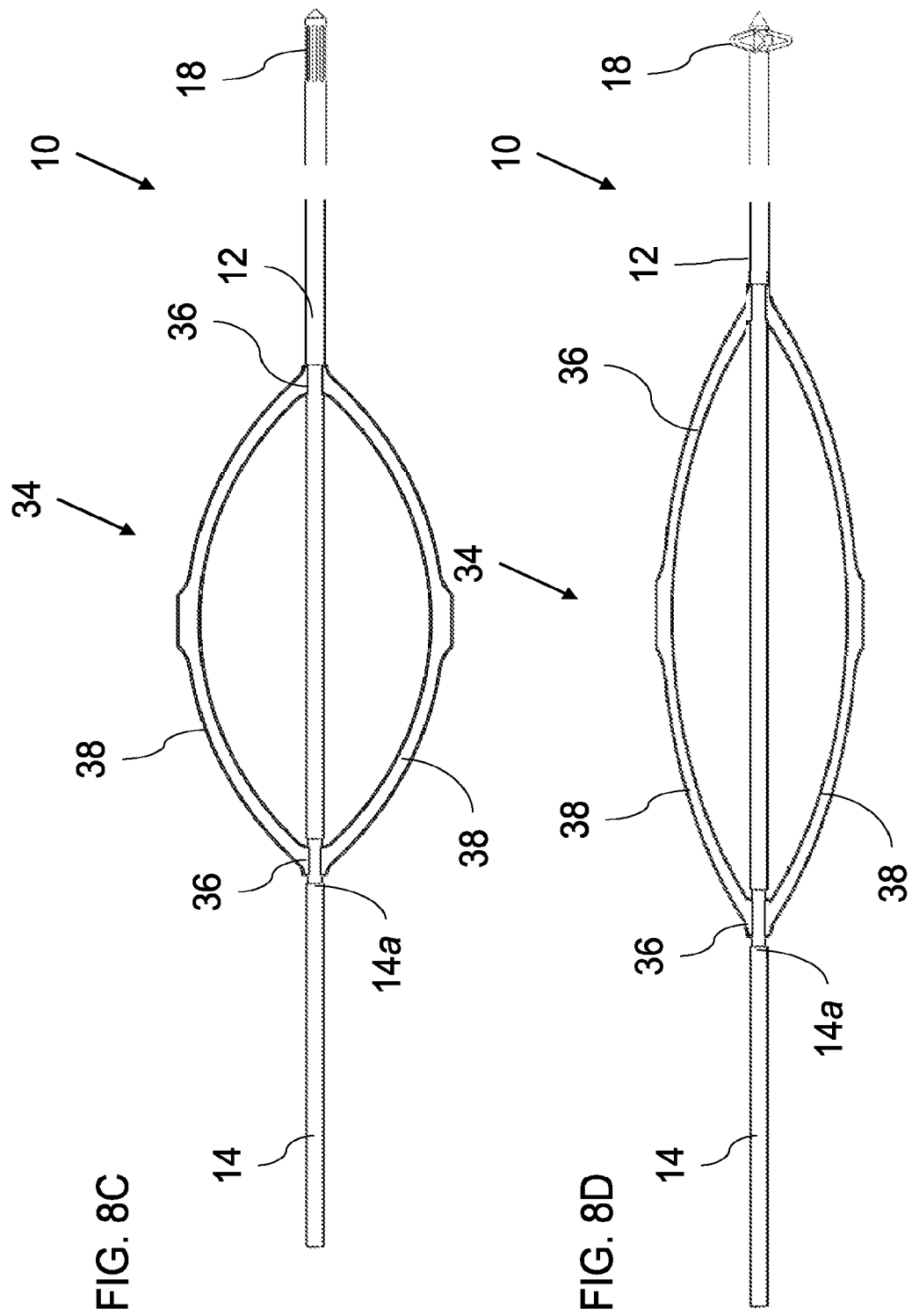

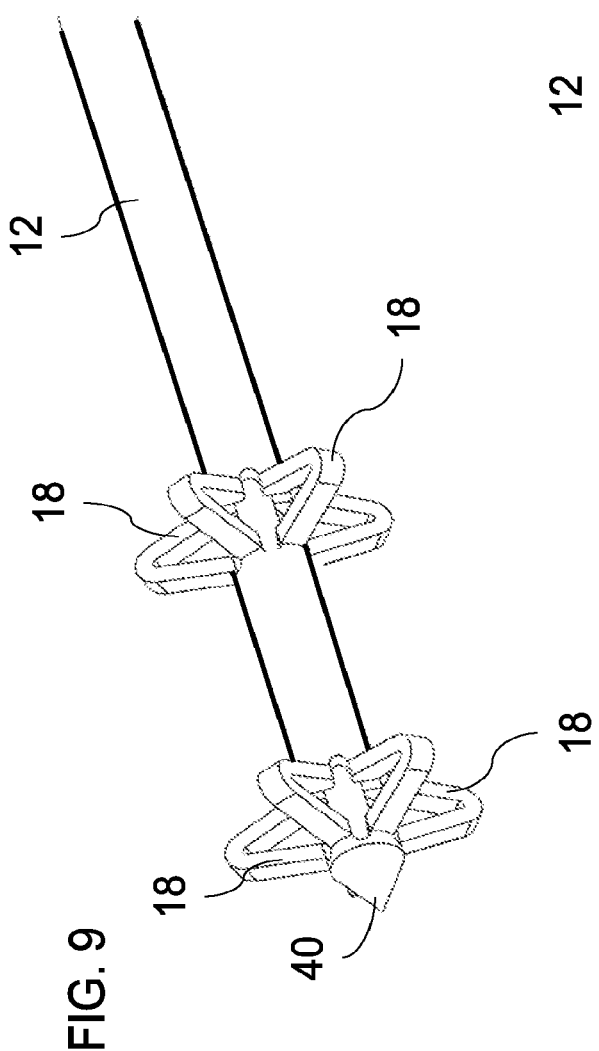
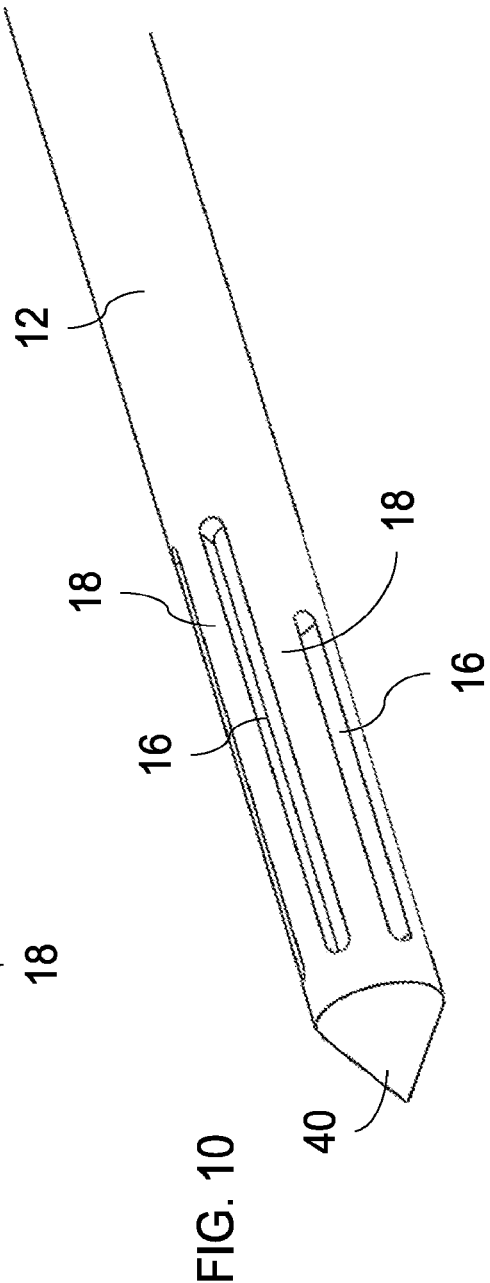

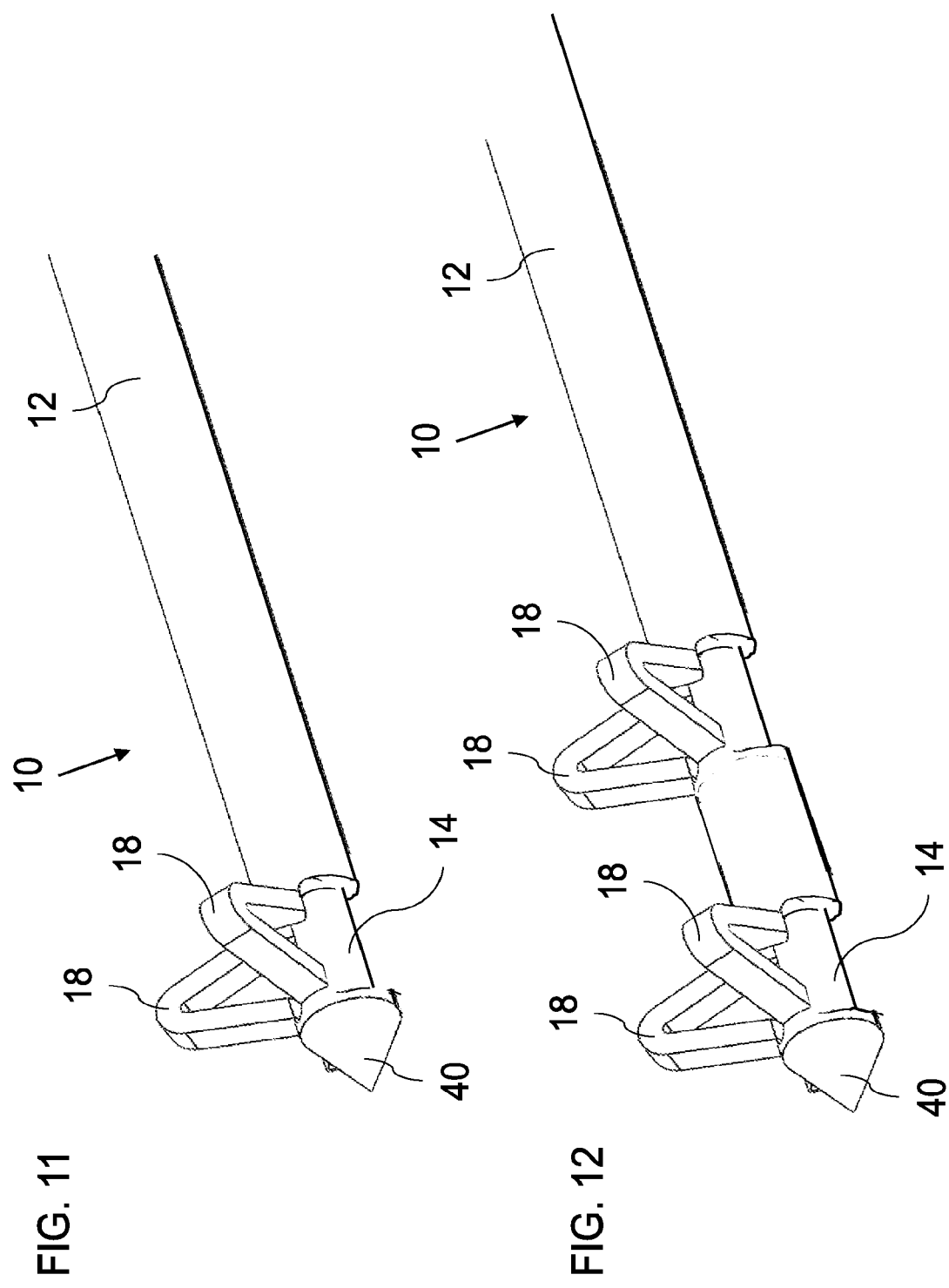

STIFF GUIDE WIRE WITH ANCHORING CONFIGURATION

FIELD AND BACKGROUND OF THE INVENTION

The present invention relates to surgical devices and methods and, in particular, it concerns a stiff guide wire with a selectively deployable anchoring configuration for use in various surgical procedures.

In various fields of surgery, such as minimally invasive spinal surgery (MISS), a sequence of steps need to be performed at an accurately defined location within the body which is not directly visible to the surgeon. In order to ensure correct placement of each tool and/or implant that is introduced into the body to perform one of the required steps, a stiff guide wire (referred to as a "Kirschner wire" or "K-wire") is often used. The guide wire is first introduced and positioned with its end at a target location within the body, typically by use of fluoroscopy or other real-time imaging modalities, and the guide wire is then used as a guide rail for subsequently introduced tools and/or implants, often introduced "over-the-wire" (OTW), to ensure that they reach the correct target tissue. Accidental displacement of the guide wire during a procedure, when immediately noticed, leads to significant delay in the procedure while the placement procedure is repeated. Such displacement may adversely affect the outcome of a procedure, and in some cases, poses an immediate risk of perforation or other damage to sensitive organs or tissues.

In some cases, such as in intervertebral procedures, the tissue into which the guide wire is inserted is soft tissue which does not provide strong retention of the guide wire. In such applications, there is an increased risk of the guide wire being displaced axially as a result of forces inadvertently transferred to the guide wire during introduction or removal of tools or implants along the wire. Additionally, and even in cases where anchoring of the guide wire is in hard tissue, many OTW procedures involve the use of reamers, drills or other tools for removing tissue surrounding at least part of the guide wire, thereby reducing the length of the guide wire which is in direct contact with tissue to provide anchoring. In all such cases, loss of placement of the guide wire during a procedure is a common complication which is at least an inconvenience and cause of delay for the surgeon, and may potentially be dangerous.

SUMMARY OF THE INVENTION

The present invention is a stiff guide wire with a selectively deployable anchoring configuration for use in various surgical procedures.

According to the teachings of an embodiment of the present invention there is provided, a device comprising: (a) a tube having an internal channel; (b) a central rod deployed in close-fitting sliding engagement within the tube, a distal end of the tube being in rigid mechanical engagement or rigid interconnection with a distal end of the central rod, wherein a region of the tube is longitudinally slotted to form a plurality of deflectable strips so that advancing of the tube relative to the central rod causes outward deflection of the deflectable strips to form an anchoring configuration, and wherein the central rod and the tube together define a stiff guide wire having a length-to-width ratio in excess of 100:1.

According to a further feature of an embodiment of the present invention, an external diameter of the guide wire is in the range of 1-3 millimeters.

According to a further feature of an embodiment of the present invention, the region of the tube has an external diameter, and wherein the deflectable strips deflect outwards to span at least 2.5 times the external diameter.

According to a further feature of an embodiment of the present invention, each of the deflectable strips is formed with a thinned deflection region that lies between a proximal portion and a distal portion of the deflectable strip, the outward deflection generating bending of the deflectable strips in the deflection regions so that the proximal portion and the distal portion of each deflect-able strip form an acute angle therebetween.

According to a further feature of an embodiment of the present invention, the deflectable strips are configured such that the bending of the deflectable strips occurs as a plastic deformation.

According to a further feature of an embodiment of the present invention, a length of the proximal portion differs from a length of the distal portion for at least one of the deflectable strips.

According to a further feature of an embodiment of the present invention, there is also provided a detachable actuator configured for engagement with a proximal portion of the tube and with the central rod, the detachable actuator being responsive to a manually applied force to advance the tube relative to the central rod, the detachable actuator being detachable from the guide wire so as to make the guide wire accessible for over-the-wire deployment of a tool or implant.

According to a further feature of an embodiment of the present invention, the stiff guide wire terminates in a pointed or chamfered tip.

According to a further feature of an embodiment of the present invention, the region slotted with slots of differing length so as to generate deflectable strips of differing lengths.

According to a further feature of an embodiment of the present invention, the region slotted with an asymmetric arrangement of slots so as to generate an asymmetric arrangement of deflectable strips.

There is also provided according to the teachings of an embodiment of the present invention, a system comprising the aforementioned device and at least one surgical tool having a bore for over-the-wire deployment, wherein the device is sized to allow over-the-wire advancing of the surgical tool with the device passing through the bore.

There is also provided according to the teachings of an embodiment of the present invention, a method for performing a surgical procedure on target tissue in the body of a patient, the method comprising the steps of: (a) creating an access opening through external tissue of the body; (b) positioning the guide wire of claim 1 extending through the access opening so that a distal tip of the guide wire is located in the target tissue and a proximal end of the guide wire projects from the body; (c) advancing the tube relative to the central rod so as to outwardly deflect the deflectable strips, thereby anchoring the guide wire in the target tissue; (d) introducing at least one tool or implant along the guide wire so as to bring at least part of the tool or the implant to a location within the target tissue; (e) retracting the tube relative to the central rod so as to retract the deflectable strips and release anchoring of the guide wire in the target tissue; (f) removing the guide wire from the body; and (g) closing the access opening.

According to a further feature of an embodiment of the present invention, the tool or implant is a tissue removal tool, the method further comprising employing the tissue removal tool to remove at least some of the target tissue adjacent to the guide wire proximal to the anchoring configuration.

According to a further feature of an embodiment of the present invention, the target tissue is at least part of an intervertebral disc.

According to a further feature of an embodiment of the present invention, the target tissue is at least part of a vertebra.

BRIEF DESCRIPTION OF THE DRAWINGS

The invention is herein described, by way of example only, with reference to the accompanying drawings, wherein:

FIG. 1 is a disassembled isometric view of a device according to the teachings of an embodiment of the present invention for use as a stiff guide wire with a selectively deployable anchoring configuration for use in surgical procedures;

FIGS. 2A and 2B are assembled isometric views of the device of FIG. 1 showing the anchoring configuration in a non-deployed state and a deployed state, respectively;

FIGS. 3A and 3B are enlarged partial isometric views of the device of FIG. 1 showing the anchoring configuration in a non-deployed state and a deployed state, respectively;

FIG. 4A is an isometric view of a tip portion of a variant implementation of the device of FIG. 1 illustrating a deflection limiting projection for the anchoring configuration;

FIGS. 4B and 4C are schematic axial cross-section views taken through a tip portion of variant implementations of the device of FIG. 1 illustrating how a given extent of radial opening of the anchoring configuration may be achieved using shorter and longer deflectable strips, respectively;

FIGS. 4D and 4E are views similar to FIGS. 4-B and 4C illustrating variant implementations of deflectable strips with asymmetrically deployed flexible regions;

FIG. 6A is an isometric view of a proximal end of the device of FIG. 1 illustrating an optional locking configuration;

FIGS. 6B and 6C are axially cut-away views of the locking configuration of FIG. 6A showing the device in a pre-deployment (retracted) state and a deployed state, respectively;

FIG. 8A is an isometric view of the device of FIG. 1 showing a detachable actuator attached to the device;

FIG. 8B is an enlarged view of the region of FIG. 8A showing the detachable actuator;

FIGS. 8C and 8D are partial side views illustrating the device and actuator of FIG. 8A prior to and after operation of the actuator, respectively;

FIG. 9 is an isometric view of a tip portion of a further variant implementation of the device of FIG. 1 showing a pair of spaced-apart anchoring configurations in a deployed state;

FIG. 10 is an isometric view of a tip portion of a further variant implementation of the device of FIG. 1 showing an implementation with non-uniform lengths of deflectable strips;

FIG. 11 is an isometric view of a tip portion of a further variant implementation of the device of FIG. 1 showing an implementation with non-symmetric deployment of deflectable strips; and FIG. 12 is an isometric view of a tip portion of a still-further variant implementation of the device of FIG. 1 which employs non-symmetric deployment of deflectable strips in two spaced-apart anchoring configurations.

DESCRIPTION OF THE PREFERRED EMBODIMENTS

Figure 5A:
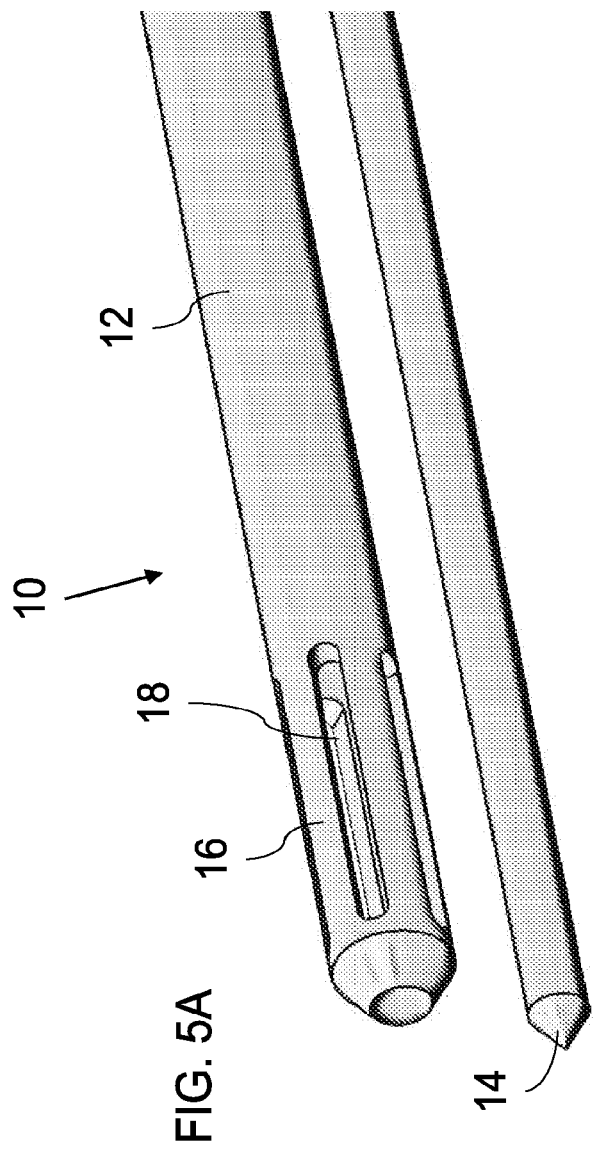
FIGS. 5A and 5B are disassembled and assembled isometric views, respectively, of a tip portion of a variant implementation of the device of FIG. 1.

The present invention is a stiff guide wire with a selectively deployable anchoring configuration for use in various surgical procedures.

The principles and operation of guide wires according to the present invention may be better understood with reference to the drawings and the accompanying description.

Referring now to the drawings, FIGS. 1-12 show various implementations of a device 10 which serves as a stiff guide wire for surgical procedures. In general terms, device 10 includes a metal tube 12 having an internal channel, and a metal central rod 14 deployed in close-fitting sliding engagement within tube 12. A distal end of tube 12 is in rigid mechanical engagement, or rigid interconnection, with a distal end of central rod 14. A region of tube 12 is longitudinally slotted (slots 16 best seen in FIGS. 3A, 5A, 7 and 10) to form a plurality of deflectable strips 18 so that advancing of tube 12 relative to central rod 14 causes outward deflection of deflectable strips 18 to form an anchoring configuration, as seen in FIGS. 2B and 3B. Central rod 14 and tube 12 together define a stiff guide wire preferably having a length-to-width ratio in excess of 100:1.

The term "stiff" is used herein in the description and claims to distinguish the device of the present invention from other classes of devices used in different fields, such as in vascular surgery, that are referred to as "guide wires", but relate to highly flexible devices designed for navigating tortuous paths through the vascular system. The guide wires of the present invention may be somewhat flexible, but are referred to as "stiff" in the sense that they are not typically deflected through more than about 45 degrees under normal conditions of use, and maintain a tendency to return to a fully straightened state when released. The "stiff guide wire" of the present invention thus corresponds to what is generally referred to as an intra-operative Kirschner wire or K-wire. Additional parameters which characterize certain preferred implementations of the guide wire of the present invention include one or more of: an external diameter in the range of 1-3 millimeters, and most preferably 1.5-2 millimeters; an overall length of at least 20 centimeters, and typically 30-50 centimeters; and the aforementioned length-to-width ratio of at least 100:1, and frequently at least 200:1.

Figure 7:
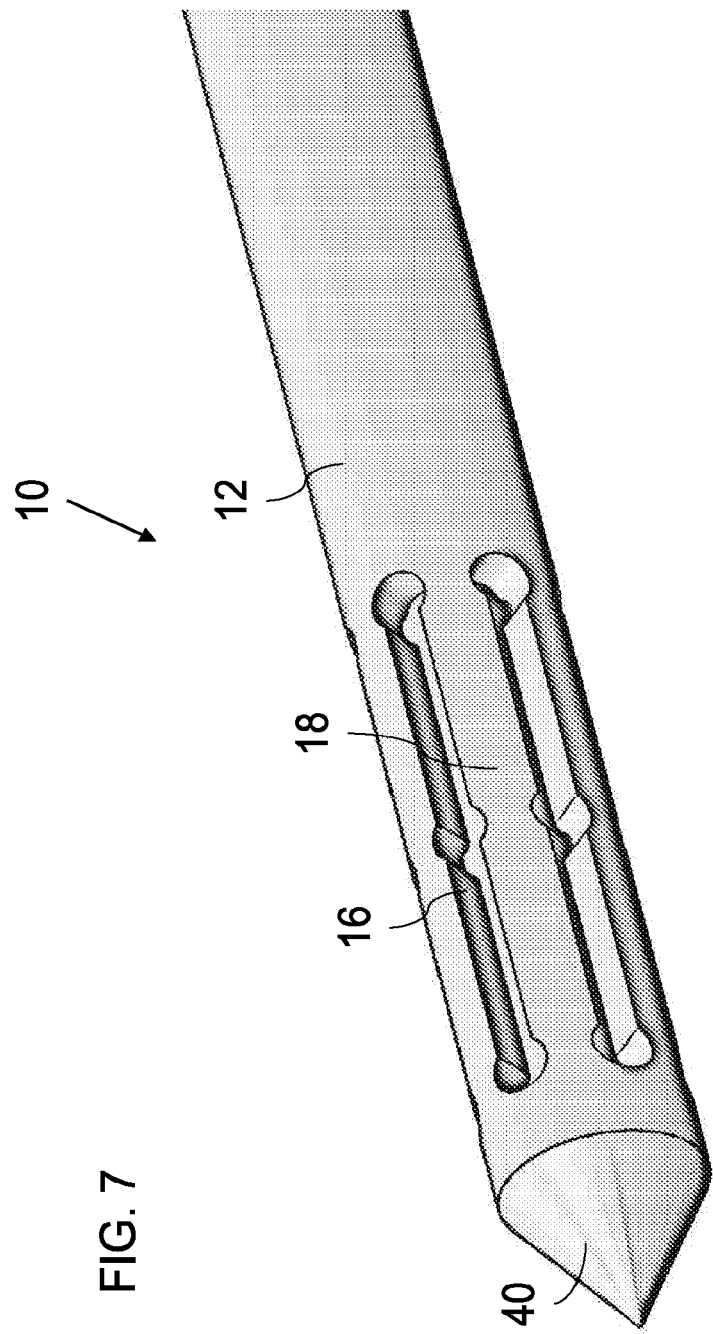
FIG. 7 is an isometric view of a tip portion of a further variant implementation of the device of FIG. 1.

Optionally, some or all of deflectable strips 18 are formed with a defined deflection region 20 that lies between a proximal portion 22 and a distal portion 24 of the deflectable strip. Deflection region 20 may be defined by localized thinning of strip 18, either in the thickness dimension of tube 12 or by shaping slots 16 as illustrated in FIG. 7 to locally reduce the width of strips 18, or may be defined by a choice of material properties and geometry of deflection which tends to cause localized buckling of the strip in deflection region 20. In all of these cases, the outward deflection of strips 18 preferably results in bending of the strips in deflection regions 20 so that proximal portion 22 and distal portion 24 of each strip form between them an acute angle. This geometry presents proximal and distal surfaces which are at a high angle to the extensional axis of the guide wire, preferably in excess of 60 degrees and typically over 70 degrees, which are highly effective in engaging soft tissue so as to oppose both proximal and distal migration of the guide wire. Additionally, or alternatively, the relatively "pointed" configuration formed by an acute deflection angle at deflection regions 20 tend to be effective at penetrating into adjacent tissue around the guide wire, thereby engaging a larger volume of tissue to provide reactive forces opposing axial migration of the guide wire.

The deflection region 20 typically divides strips 18 into two equal parts, forming symmetrical V-shaped deflected forms. In some cases, it may be preferable to form some or all of strips 18 with a deflection region 20 that is off-center, so that one portion is longer than the other. This results in a directional asymmetric V-shape or saw-tooth shape, deflected either in a distal direction (FIG. 4D) or a proximal direction (FIG. 4E), which may be useful where retention of the guide wire in one direction is particularly critical, for example, to oppose distal migration of a guide wire beyond a far side of an intervertebral disc, where sensitive tissues are located. Alternatively, strips such as those of FIGS. 4D and 4E may be combined in a single device, for example, with alternating strips being inclined distally and proximally. If tube 12 is advanced further, an undercut saw-tooth shape may be formed which, in some cases, may provide further enhanced retention.

The lateral dimensions of the deployed anchoring configuration are determined primarily by the length of slots 16 and strips 18, and may be chosen according to the requirements of a given intended application. In certain particularly preferred implementations, deflectable strips 18 deflect outwards to span at least 2.5 times the external diameter of tube 12, and in many case at least 3 times the external diameter.

It should be noted that the dimensions of the deflectable strips 18 are not necessarily uniform. For example, as illustrated in FIG. 10, a pair of relatively long slots 16 may define a longer strip 18 which opens to a larger radial extent while certain shorter slots define a shorter strip which opens to a smaller radial extent. It will be noted that the range of motion of tube 12 relative to central rod 14 is here defined by a fully deflected state of the shortest strip 18, while the longer strip(s) 18 may open to a lesser angle. A combination of relatively longer and shorter strips 18 may be useful in applications where the guide wire is to be deployed in soft tissue adjacent to hard tissue. In such a case, relatively small strips may be deployed facing the hard tissue surface so as to avoid applying excessive force against the hard tissue surface which might cause an unwanted opposite displacement of the device.

Similarly, the arrangement of strips 18 circumferentially around tube 12 need not be symmetrical and, in some cases, broad slots 16 or cut-outs may be provided so that some angular extent around tube 12 does not include deflectable strips. One such example is illustrated in FIG. 11, where the lower side as illustrated is formed without deflectable strips.

In some cases, even where the strips 18 are all of the same length, it may be desired to limit the range of motion of tube 12 relative to central rod 14 in order to limit the angular deflection of the deflection regions. This may be achieved as illustrated in FIG. 4A by providing a deflection-limiting projection 26, typically in place of one of strips 18 which serves as a spacer limiting how far tube 12 can be advanced until deflection-limiting projection 26 reaches the opposite end of the cut-out region and comes into abutment so as to prevent further deflection. FIGS. 4B and 4C illustrate schematically how the same overall retention footprint represented by a transverse span "H" can be achieved either using relatively short strips 18 and high-angle deflection (FIG. 4B) or relatively long strips 18 at relatively low-angle deflection (FIG. 4C), where the extent of deflection is limited, for example, by a deflection-limiting projection as illustrated in FIG. 4A. Configurations such as those of FIGS. 4D and 4E may also employ deflection limiting features where it is desired to define a final position for example as shown here, with the distal or proximal portion of a strip roughly perpendicular to the length of the guide wire rather than continuing to an undercut saw-tooth configuration.

Tube 12 and central rod 14 may be formed from any suitable material or combination of materials. Typically, they are formed from biocompatible metal (including metal alloys) such as titanium, titanium alloy or stainless steel, although other biocompatible materials or combinations of materials may also be used.

In order to accommodate over-the-wire functionality, it is an important feature of various particularly preferred implementations of the present invention that the proximal end of the guide wire allows unimpeded access without any significant increase in dimensions from the overall tube external diameter to allow threading of tools and devices "over the wire." A number of preferred features of certain implementations of the present invention are particularly adapted to facilitating this functionality, as will now be described.

In some cases, the choice of materials, dimensions and deflection angles are such that bending of deflectable strips 18 takes the strips beyond the elastic limit of the material and occurs as a plastic deformation. This is believed to provide advantages in certain applications as the strips then remain in their deflected state without springing back to their original state. This allows the device to be anchored and remain anchored without requiring a locking mechanism to maintain the deployed state. Since each guide wire is typically a single-use disposable device, the deflection mechanism is not normally subjected to repeated deployment and retraction, and the plastic deformation typically does not compromise the structural integrity of the device over a single cycle, or even a small number of repeated cycles.

Alternatively, or additionally, a highly compact locking mechanism may be provided such as is exemplified in FIGS. 6A-6C. In this case, a rear edge of tube 12 is slotted to form a leaf spring 28 terminating at a detent 30 which engages one or more indents 32 formed in central rod 14. The detent 30 and an indent 32 are positioned such that they click into position in the fully deployed anchoring state (FIG. 6C), thereby reliably maintaining the deployed state even where the deformation occurs elastically. The locking effect is overcome by applying sufficient axial force, thereby allowing retraction of the anchoring configuration for removal of the guide wire. A second indent 32 defines a fully-retracted retention position (FIG. 613), thereby protecting the device from inadvertent premature deployment and/or ensuring that the retracted state is maintained during removal of the device. The locking mechanism as shows is implemented within the overall external diameter of the guide wire, and thus does not impinge on over-the-wire applications.

FIGS. 8A-8D illustrate a further preferred option according to which a detachable actuator 34 is provided for engagement with a proximal portion of tube 12 and with central rod 14. Detachable actuator 34 is responsive to a manually applied force to advance tube 12 relative to central rod 14, and is detachable from the guide wire after use so as to make the proximal part of the guide wire accessible for over-the-wire deployment of a tool or implant. In the specific non-limiting example illustrated in FIGS. 8A-8D, actuator 34 has two clip portions 36, one of which engages the proximal end of tube 12 and the other of which engages a step 14a of outer diameter similar to the outer diameter of tube 12 formed in the proximal portion of central rod 14 that extends beyond the tube. The increased diameter proximal region of central rod 14 preferably has a diameter no larger than that of tube 12 such that it does not impede use of the guide wire for over-the-wire applications. Two arched elements 38 bridge bilaterally between clip portions 36 so that manual squeezing together of arched elements 38 generates a corresponding outwards displacement of clip portions 36 away from each other, thereby advancing tube 12 distally relative to central rod 14. After deployment, actuator 34 can be unclipped from the guide wire, leaving the guide wire available for unimpeded OTW usage.

Detachable actuator 34 is only one example of a wide range of detachable actuators which may be used to advance tube 12 so as to deploy the anchoring configurations of the present invention, Various features may be formed on one or both of tube 12 and central rod 14 to facilitate interfacing of the guide wire with a given actuating instrument. Such features may include indents, protrusions and any other such features, which are preferably included within the overall diameter profile of the guide wire or project therefrom by less than 1 wire diameter, thereby facilitating OTW functionality. Optionally, the external surfaces of the proximal portion of tube 12 and/or the portion of central rod 14 which extends beyond the tube may be roughened to improve grip. In some cases, a detachable actuator may perform both the deployment and retraction of the anchoring configuration. In some cases, it has been found that relatively small force is required for retraction of the anchoring configuration, and that this may be achieved simply by manual retraction of tube 12 while holding still central rod 14, as part of a manual guide wire removal step.

As mentioned earlier, the distal end of tube 12 should be in rigid mechanical engagement, or rigid interconnection, with the distal end of central rod 14, in order to allow tension on central rod 14 to provide the counterforce for the compression of strips 18 by advancing tube 12 which leads to deployment of the anchoring mechanism. According to a first non-limiting implementation as illustrated in FIG. 1, central rod 14 is formed with an enlarged distal tip 40 which has an outer diameter similar to that of tube 12. When central rod 14 is inserted through tube 12 from the distal end, distal tip 40 comes into abutment with the distal edge of tube 12 to provide rigid mechanical engagement suitable for providing the aforementioned counterforce to deploy the anchoring mechanism.

Figure 5B:
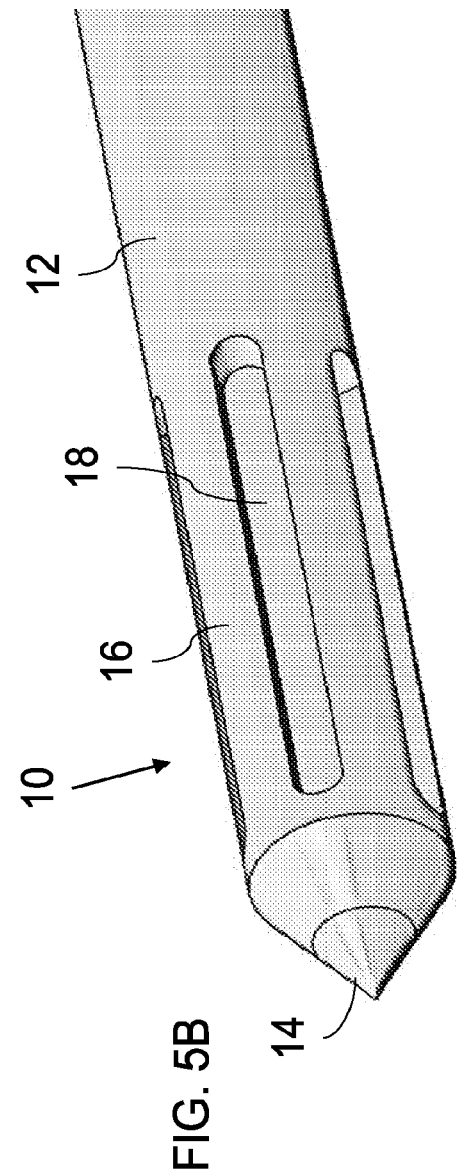

An alternative non-limiting implementation is illustrated in FIGS. 5A and 5B. In this case, the distal end of central rod. 14 is not enlarged, and tube 12 and central rod 14 are rigidly interconnected at the tip region. The interconnection is most preferably by welding, but may alternatively be implemented using any other suitable technique, including but not limited to, threaded attachment and crimping.

Depending on the intended application and the diameter of the guide wire, it may be preferable to implement the distal tip as either a pointed tip or at least having a diameter-reducing chamfer at the tip. According to the implementation of FIG. 1, the tip geometry is implemented through appropriate shaping of distal tip 40. In the option of FIGS. 5A and 5B, the final tip shape is typically formed by a combination of the geometry of both the tube and the central rod, which are carefully aligned with each other prior to interconnection.

In the examples discussed so far, the anchoring configuration is typically in proximity to the distal end of the guide wire. In quantitative terms, this may be defines by the fact that the deployed anchoring configuration is located within a distance from the distal tip of the guide wire which is no more than roughly twice the maximum diameter of the anchoring configuration when deployed. It should be noted however that the present invention is not limited to such distal positioning of the anchoring configuration, and that, the anchoring configuration, or an additional anchoring configuration, may be provided at any desired location along the guide wire. By way of example, FIG. 9 illustrates a case where two anchoring configurations are disposed at spaced-apart locations along the distal portion of the guide wire. Such a configuration may be particularly useful in application in which a tissue volume beyond the operative target tissue is available for anchoring of the guide wire. FIG. 12 illustrates a further variant which combines the double spaced-apart anchoring configurations with the asymmetrical one-sided deployment of FIG. 11.

Turning now to the use of the present invention, corresponding to a method for performing a surgical procedure on target tissue in the body of a patient, such a procedure typically begins with creating an access opening through external tissue of the body, which is preferably a percutaneous incision for a minimally-invasive procedure. The guide wire of the present invention is the positioned so as to extend through the access opening so that a distal tip of the guide wire is located in the target tissue and a proximal end of the guide wire projects from the body. Placement of the guide wire is typically performed using various imaging modalities and/or navigation-assisting tools, as is well known in the art.

Once correct alignment of the guidewire has been achieved, tube 12 is advanced relative to central rod 14, for example, by squeezing removable actuator 34 from the state of FIG. 8C to that of FIG. 8D, or by operation of some other suitable removable actuating device, so as to outwardly deflect deflectable strips 18, thereby anchoring the guide wire in the target tissue. The actuator device is then preferably removed, leaving the guide wire unobstructed and ready for us.

The surgical procedure is then continued by introducing at least one tool or implant along the guide wire, typically threaded over the guide wire in an "over-the-wire" configuration, so as to bring at least part of the tool or the implant, to a location within the target tissue.

After completion of the operations to be performed using the guide wire, tube 12 is retracted relative to central rod 14 so as to retract (straighten) deflectable strips 18 and release anchoring of the guide wire in the target tissue. The guide wire is then removed from the body. The access opening (incision) is then closed, for example using one or more sutures, to complete the surgical procedure.

The present invention is applicable to a wide range of surgical procedures including, but not limited to, MISS surgery of all kinds. A first subset of applications relate to procedures where the target tissue is at least part of an intervertebral disc, including but not limited to, intervertebral fusion procedures. In such cases, the tools introduced over the wire typically include a sequence of reamers of different sizes and endplate preparation tools. In some cases, an intervertebral cage or other implant may also be introduced over the wire.

Another subset of applications relate to procedures in which the target tissue is at least part of a vertebra, which may be part of the vertebral body or a pedicle. In a non-limiting example of deployment of a pedicle screw, the guide wire is typically inserted along a narrow bore drilled into the pedicle, and a sequence of different size cannulated drills are introduces over the wire, until the opening is correctly sized for introduction of the pedicle screw, which may also be introduced over the wire.

It will be appreciated that the above descriptions are intended only to serve as examples, and that many other embodiments are possible within the scope of the present invention as defined in the appended claims.

The invention claimed is:

1. A device comprising:
a tube having an internal channel;
a central rod deployed in close-fining sliding engagement within said internal channel of said tube, a distal end of said tube interconnected with a distal end of said central rod;
wherein a region of said tube is longitudinally slotted to form a plurality of deflectable strips so that advancement of said tube relative to said central rod causes outward deflection of said deflectable strips to form an anchoring configuration, and wherein said central rod and said tube together define a stiff guide wire; and
a detachable actuator configured for engagement with a proximal portion of said tube and with said central rod, said detachable actuator being responsive to a manually applied force to advance said tube relative to said central rod, said detachable actuator being detachable from said guide wire so as to make said guide wire accessible for over-the-wire deployment of a tool or implant.

2. The device of claim 1, wherein an external diameter of said guide wire is in the range of 1-3 millimeters.

3. The device of claim 1, wherein said region of said tube has an external diameter, and wherein said deflectable strips deflect outwards to span at least 2.5 times said external diameter.

4. The device of claim 1, wherein each of said deflectable strips is formed with a thinned deflection region that lies between a proximal portion and a distal portion of said deflectable strip, said outward deflection generating bending of said deflectable strips in said deflection regions so that said proximal portion and said distal portion of each deflectable strip form an acute angle therebetween.

5. The device of claim 4, wherein said deflectable strips are configured such that said bending of said deflectable strips occurs as a plastic deformation.

6. The device of claim 4, wherein a length of said proximal portion differs from a length of said distal portion for at least one of said deflectable strips.

7. The device of claim 1, wherein said stiff guide wire terminates in a pointed or chamfered tip.

8. The device of claim 1, wherein said region slotted with slots of differing length so as to generate deflectable strips of differing lengths.

9. The device of claim 1, wherein said region slotted with an asymmetric arrangement of slots so as to generate an asymmetric arrangement of deflectable strips.

10. A system comprising the device of claim 1 and at least one surgical tool having a bore for over-the-wire deployment, wherein said device is sized to allow over-the-wire advancing of said surgical tool with said device passing through said bore.

11. A method for performing a surgical procedure on target tissue in the body of a patient, the method comprising the steps of:

providing a device comprising a tube having an internal channel, a central rod deployed in close-fitting sliding engagement within said internal channel of said tube, a distal end of said tube interconnected with a distal end of said central rod, wherein a region of said tube is longitudinally slotted to form a plurality of deflectable strips so that advancement of said tube relative to said central rod causes outward deflection of said deflectable strips to form an anchoring configuration, and wherein said central rod and said tube together define a stiff guide wire;

providing a detachable actuator configured for engagement with a proximal portion of said tube and with said central rod, said detachable actuator being responsive to a manually applied force to advance said tube relative to said central rod, said detachable actuator being detachable from said guide wire so as to make said guide wire accessible for over-the-wire deployment;

creating an access opening through external tissue of the body;

positioning the guide wire extending through the access opening so that a distal tip of the guide wire is located in the target tissue and a proximal end of the guide wire projects from the body;

advancing said tube relative to said central rod so as to outwardly deflect said deflectable strips, thereby anchoring the guide wire in the target tissue;

introducing at least one tool or implant along the guide wire so as to bring at least part of the tool or the implant to a location within the target tissue;

retracting said tube relative to said central rod so as to retract said deflectable strips and release anchoring of the guide wire in the target tissue;

removing the guide wire from the body; and closing the access opening.

12. The method of claim 11, wherein said tool or implant is a tissue removal tool, the method further comprising employing said tissue removal tool to remove at least some of said target tissue adjacent to the guide wire proximal to said anchoring configuration.

13. The method of claim 11, wherein said target tissue is a least part of an intervertebral disc.

14. The method of claim 11, wherein said target tissue is a least part of a vertebra.

15. A device comprising:
a tube having an internal channel;
a central rod deployed in close-fitting sliding engagement within said internal channel of said tube, a distal end of said tube interconnected with a distal end of said central rod;
wherein a region of said tube is longitudinally slotted to form a plurality of deflectable strips so that advancement of said tube relative to said central rod causes outward deflection of said deflectable strips to form an anchoring configuration, and wherein said central rod and said tube together define a stiff guide wire; and
wherein each of said deflectable strips is formed with a thinned deflection region that lies between a proximal portion and a distal portion of said deflectable strip, said outward deflection generating bending of said deflectable strips in said deflection regions so that said proximal portion and said distal portion of each deflectable strip form an acute angle therebetween.

16. The device of claim 15, wherein said deflectable strips are configured such that said bending of said deflectable strips occurs as a plastic deformation.

17. The device of claim 15, wherein a length of said proximal portion differs from a length of said distal portion for at least one of said deflectable strips.

18. The device of claim 15, further comprising a second plurality of deflectable strips spaced longitudinally apart from the plurality of deflectable strips.

19. The device of claim 15, wherein said region slotted with slots of differing length so as to generate deflectable strips of differing lengths.

20. The device of claim 15, wherein said region slotted with an asymmetric arrangement of slots so as to generate an asymmetric arrangement of deflectable strips.

21. The device of claim 15, wherein said region slotted with an symmetric arrangement of slots so as to generate an symmetric arrangement of deflectable strips.

* * * * *